US011727564B2

(12) United States Patent
Ceballos Lentini et al.

(10) Patent No.: US 11,727,564 B2
(45) Date of Patent: *Aug. 15, 2023

(54) SYSTEMS AND METHODS TO PROCESS ELECTRONIC IMAGES TO PROVIDE IMAGE-BASED CELL GROUP TARGETING

(71) Applicant: PAIGE.AI, Inc., New York, NY (US)

(72) Inventors: Rodrigo Ceballos Lentini, Flemington, NJ (US); Christopher Kanan, Pittsford, NY (US); Belma Dogdas, Ridgewood, NJ (US)

(73) Assignee: Paige.AI, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/815,671

(22) Filed: Jul. 28, 2022

(65) Prior Publication Data
US 2022/0366563 A1   Nov. 17, 2022

Related U.S. Application Data

(63) Continuation of application No. 17/406,002, filed on Aug. 18, 2021, now Pat. No. 11,436,727, which is a
(Continued)

(51) Int. Cl.
 *G06T 7/00* (2017.01)
 *G06T 7/11* (2017.01)
 (Continued)

(52) U.S. Cl.
 CPC ...... *G06T 7/0012* (2013.01); *G06F 18/23213* (2023.01); *G06N 20/00* (2019.01);
 (Continued)

(58) Field of Classification Search
 CPC .............. G06T 7/0012; G06T 7/11; G06T 2207/20081; G06T 2207/30024;
 (Continued)

(56) References Cited

U.S. PATENT DOCUMENTS

2005/0165290 A1  7/2005  Kotsianti et al.
2010/0088264 A1  4/2010  Teverovskiy et al.
(Continued)

OTHER PUBLICATIONS

Schmauch et al., "A deep learning model to predict RNA-Seq expression of tumours from whole slide images", Nat Commun. 2020; 11(1):3877, pp. 1-15 (Year: 2020).*
(Continued)

*Primary Examiner* — Nay A Maung
*Assistant Examiner* — Jose M Torres
(74) *Attorney, Agent, or Firm* — Bookoff McAndrews, PLLC (57) ABSTRACT

Systems and methods are disclosed for grouping cells in a slide image that share a similar target, comprising receiving a digital pathology image corresponding to a tissue specimen, applying a trained machine learning system to the digital pathology image, the trained machine learning system being trained to predict at least one target difference across the tissue specimen, and determining, using the trained machine learning system, one or more predicted clusters, each of the predicted clusters corresponding to a subportion of the tissue specimen associated with a target.

20 Claims, 5 Drawing Sheets

Related U.S. Application Data continuation of application No. 17/391,997, filed on Aug. 2, 2021, now Pat. No. 11,308,616.

(60) Provisional application No. 63/061,056, filed on Aug. 4, 2020.

(51) Int. Cl.
| | |
|---|---|
| *G16H 50/20* | (2018.01) |
| *G06N 20/00* | (2019.01) |
| *G06V 10/762* | (2022.01) |
| *G06V 30/19* | (2022.01) |
| *G16B 40/00* | (2019.01) |
| *G06F 18/23213* | (2023.01) |

(52) U.S. Cl.
CPC .............. *G06T 7/11* (2017.01); *G06V 10/763* (2022.01); *G06V 30/19107* (2022.01); *G16B 40/00* (2019.02); *G16H 50/20* (2018.01); *G06T 2207/20081* (2013.01); *G06T 2207/30024* (2013.01); *G06T 2207/30096* (2013.01)

(58) Field of Classification Search
CPC ............ G06T 2207/30096; G06K 9/62; G06K 9/6223; G06N 20/00; G06V 10/70; G06V 10/763; G06V 20/69; G06V 30/19107; G16B 40/00; G16H 50/20

See application file for complete search history.

(56) References Cited

U.S. PATENT DOCUMENTS

| | | |
|---|---|---|
| 2017/0262984 A1 | 9/2017 | Barnes et al. |
| 2018/0005417 A1 | 1/2018 | Schieke |
| 2020/0226462 A1 | 7/2020 | Maddison et al. |
| 2020/0258223 A1 | 8/2020 | Yip et al. |
| 2020/0272864 A1 | 8/2020 | Faust et al. |
| 2021/0018742 A1 | 1/2021 | Stumpe |
| 2021/0019342 A1 | 1/2021 | Peng et al. |
| 2021/0073986 A1 | 3/2021 | Kapur et al. |
| 2021/0166380 A1 | 6/2021 | Yip et al. |

OTHER PUBLICATIONS

Bera Kaustav; Schalper Kurt A.; Rimm David L.; Velcheti Vamsidhar; Madabhushi Anant, "Artificial intelligence in digital pathology—new tools for diagnosis and precision oncology", Nature Reviews Clinical Oncology, Nature, NY, US, NY, US , (Aug. 9, 2019), vol. 16, No. 11, doi:10.1038/s41571-019-0252-y, ISSN 1759-4774, pp. 703-715, XP036911541, Year: 2019.

Harder et al., "Tissue Phenomics for prognosis biomarker discovery in low- and intermediate-risk prostate cancer", Scientific Reports, 2018; 8: 4470, pp. 1-19, Year: 2018.

Ibrahim, "Generalized Categorisation of Digital Pathology Whole Slides using Unsupervised Learning", arXiv:2012.13955v1, pp. 1-42 (Year: 2020).

Joel Saltz et al: "Spatial Organization and Molecular Correlation of Tumor-Infiltrating Lymphocytes Using Deep Learning on Pathology Images," XP05557 4630, Year: 2018.

Vamathevan Jessica; Clark Dominic; Czodrowski Paul; Dunham Ian; Ferran Edgardo; Lee George; Li Bin; Madabhushi Anant; Shah Parantu; Spitzer Michaela; Zhao Shanrong, "Applications of machine learning in drug discovery and development", Nature Reviews Drug Discovery, Nature Publishing Group, GB, GB , (Apr. 11, 2019), vol. 18, No. 6, doi:10.1038/s41573-019-0024-5, ISSN 1474-1776, pp. 463-477, XP036796445, Year: 2019.

Yue et al., "Colorectal Cancer Outcome Prediction from H&E Whole Slide Images using Machine Learning and Automatically Inferred Phenotype Profiles", arXiv:1902.03582v2, pp. 1-11 (Year: 2019).

* cited by examiner

SYSTEMS AND METHODS TO PROCESS ELECTRONIC IMAGES TO PROVIDE IMAGE-BASED CELL GROUP TARGETING

RELATED APPLICATION(S)

This application is a continuation of and claims the benefit of priority to U.S. application Ser. No. 17/406,002, filed Aug. 18, 2021, which is a continuation of and claims the benefit of priority to U.S. application Ser. No. 17/391,997, filed Aug. 2, 2021, now U.S. Pat. No. 11,308,616, which claims priority to U.S. Provisional Application No. 63/061,056 filed Aug. 4, 2020, the entireties which are hereby incorporated herein by reference.

FIELD OF THE DISCLOSURE

Various embodiments of the present disclosure pertain generally to image-based cell group targeting and related image processing methods. More specifically, particular embodiments of the present disclosure relate to systems and methods for cell group targeting based on processing images of tissue specimens.

BACKGROUND

As personalized and targeted disease treatment options become viable, a need for fast, affordable and scalable genetic sequencing of diseases grows. Currently, one approach to this issue is to sequence large parts of tumor tissue to find usable genetic or epigenetic targets. However, the heterogeneity of most cancers means that the most common targets across all tumors in a patient are not necessarily the most effective targets. AI so, this approach does not take into consideration that there may be healthy cells in the extracted tumor which may make it more difficult to target the cancer with minimal side effects.

One solution to this problem may be to sequence smaller areas of the tumor to better understand the different mutations present across the cancer cell population in a patient, and how they differentiate from the healthy cells surrounding it. Techniques in spatial transcriptomics that may do this at a high resolution remain unproven, expensive, not scalable, and destroy the tissue.

One or more embodiments of the present disclosure may overcome the above-described problems.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for grouping cells in a slide image that share a similar target.

A method for grouping cells in a slide image that share a similar target, comprises receiving a digital pathology image corresponding to a tissue specimen, applying a trained machine learning system to the digital pathology image, the trained machine learning system being trained to predict at least one target difference across the tissue specimen, and determining, using the trained machine learning system, one or more predicted clusters, each of the predicted clusters corresponding to a subportion of the tissue specimen associated with a target.

A system for grouping cells in a slide image that share a similar target, comprising at least one memory storing instructions; and at least one processor configured to execute the instructions to perform operations comprising receiving a digital pathology image corresponding to a tissue specimen, applying a trained machine learning system to the digital pathology image, the trained machine learning system being trained to predict at least one target difference across the tissue specimen, and determining, using the trained machine learning system, one or more predicted clusters, each of the predicted clusters corresponding to a subportion of the tissue specimen associated with a target.

A non-transitory computer-readable medium storing instructions that, when executed by a processor, cause the processor to perform operations for grouping cells in a slide image that share a similar target, comprises receiving a digital pathology image corresponding to a tissue specimen, applying a trained machine learning system to the digital pathology image, the trained machine learning system being trained to predict at least one target difference across the tissue specimen, and determining, using the trained machine learning system, one or more predicted clusters, each of the predicted clusters corresponding to a subportion of the tissue specimen associated with a target.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

The present disclosure may use artificial intelligence (AI) technology to determine target clusters that may be used to differentiate clinically relevant tissue types. This may include but is not limited to: DNA, RNA, mRNA, proteins in the cell or membrane, and/or a cell's response to different treatments, such as hormones and/or drugs.

Exemplary embodiments may overcome problems with spatial transcriptomic approaches by using an artificial intelligence (AI) system applied to digital images of tissue specimens. Techniques presented herein may identify groups of similar cells. According to an exemplary embodiment, after identifying groups of similar cells, a corresponding physical tissue for each group may be sequenced individually to create a high-resolution spatial transcriptome. Alternatively, the identified groups may be used to predict biomarkers and other targets directly from the digital image using AI. This may provide an intermediate solution that would allow physicians to better understand the genetic heterogeneity across a patient's cancer by using established sequencing techniques.

The below definitions are explanatory only and are not intended to be limiting. WSIs may refer to one or more images of tissue, stained or unstained. Target(s) may refer to something that may be used to differentiate clinically relevant tissue types, including but not limited to biological cell types (e.g., stroma, vessels, macrophages, etc.), DNA, RNA, mRNA, proteins in the cell or membrane, and/or a cell's response to different hormones and/or drugs. Targeted sampling may refer to an ability to sample specific areas of a tissue that when sampled may be used to correctly infer the distribution of targets over the whole tissue. A cluster may refer to a region or collection of regions that share a target or a co-occurrence/co-expression of targets. Metadata may refer to any information related to a WSI or case (e.g., patient information, diagnostic information, tissue type, stain type, genomic sequencing, polymerase chain reaction (PCR), flow cytometry, mass spectrometry etc.). A pathology image may be any medical image that may be used to infer the genetic or epigenetic content of a specific region of tissue.

Figure 1A:
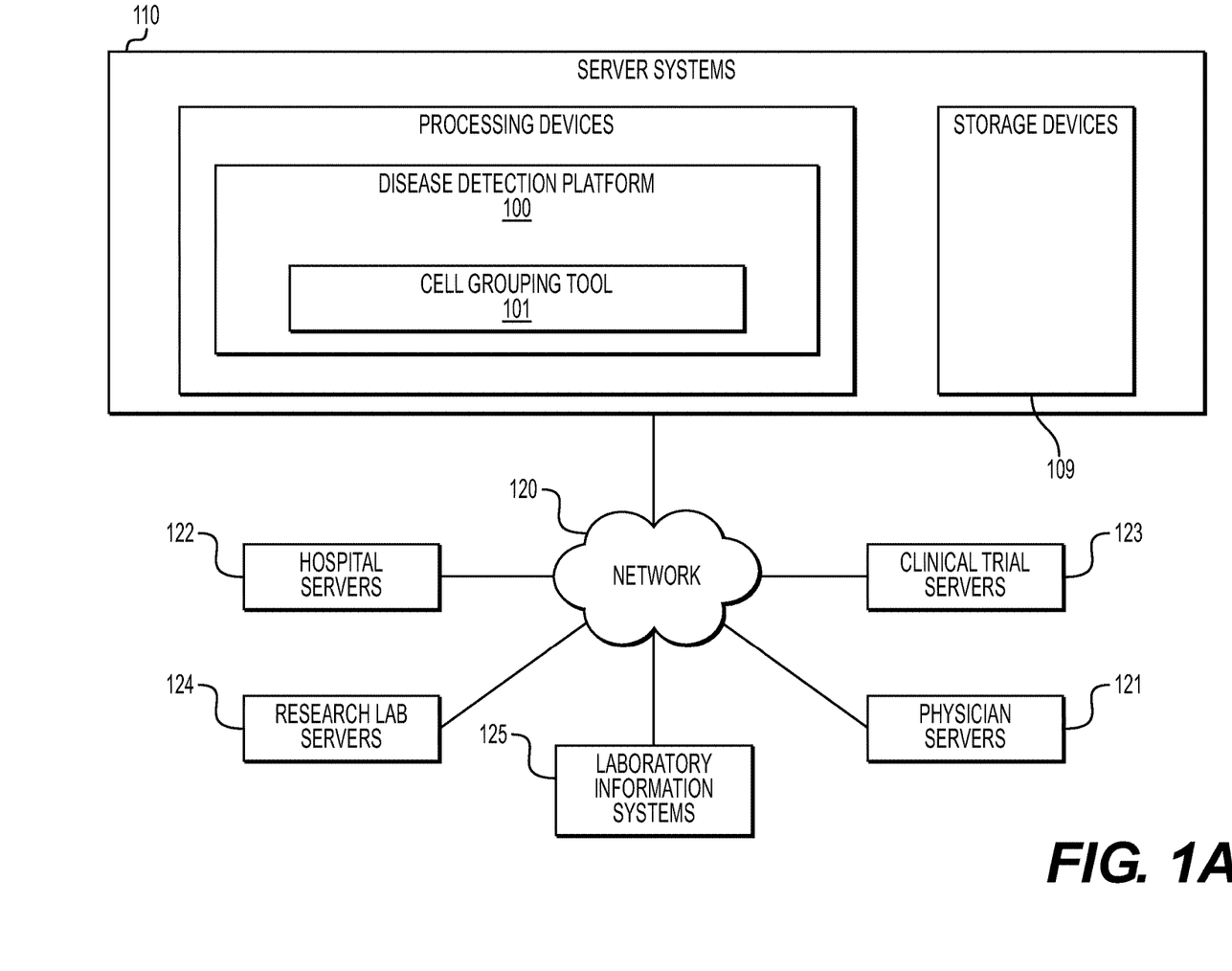
FIG. 1A illustrates an exemplary block diagram of a system and network for grouping cells in a whole slide image (WSI) that share similar targets, according to an exemplary embodiment of the present disclosure.

FIG. 1A illustrates a block diagram of a system and network for grouping cells in a WSI that share similar targets, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a cell grouping tool 101 for grouping cells in a WSI that share similar targets, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems (LIS) 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or LIS 125 refer to systems used by pathologists for reviewing the images of the slides. In hospital settings, tissue type information may be stored in a LIS 125. According to an exemplary embodiment of the present disclosure, cells in a WSI that share similar targets may be grouped without needing to access the LIS 125. Additionally, access to LIS content may be limited due to its sensitive content.

Figure 1B:
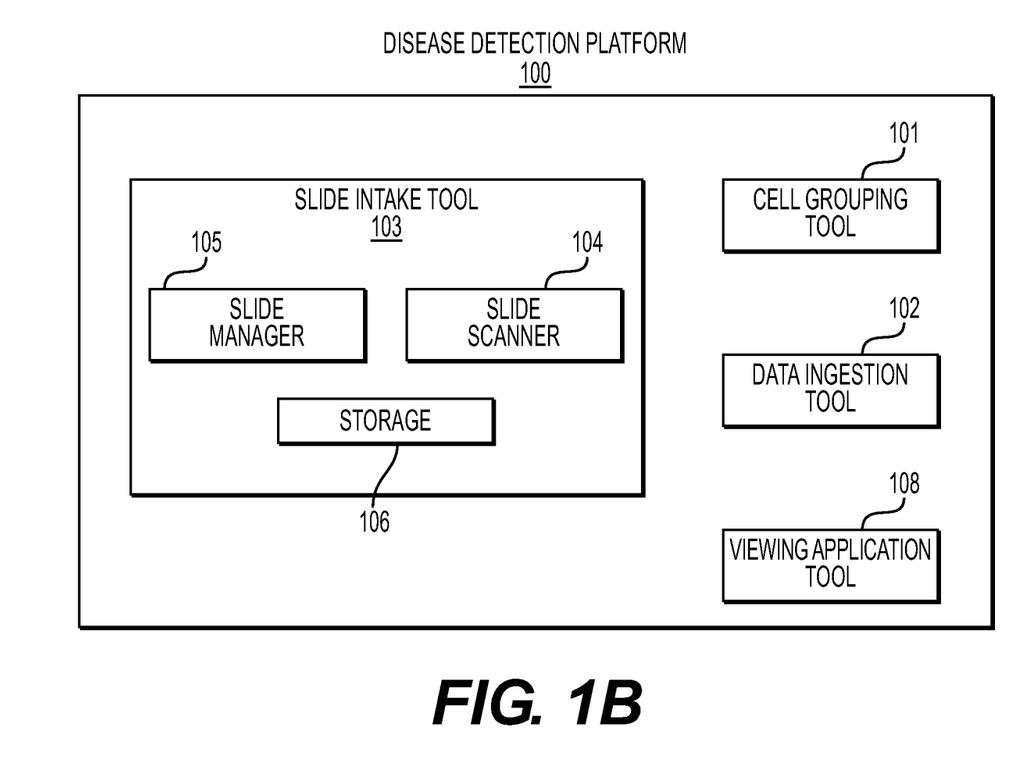
FIG. 1B illustrates an exemplary block diagram of the disease detection platform 100, according to an exemplary embodiment of the present disclosure.

FIG. 1B illustrates an exemplary block diagram of a disease detection platform 100 for grouping cells in a WSI that share similar targets, using machine learning.

Specifically, FIG. 1B depicts components of the disease detection platform 100, according to one embodiment. For example, the disease detection platform 100 may include a cell grouping tool 101, a data ingestion tool 102, a slide intake tool 103, a slide scanner 104, a slide manager 105, a storage 106, and a viewing application tool 108.

The cell grouping tool 101, as described below, refers to a process and system for grouping cells in a WSI that share similar targets, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The cell grouping tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the cell grouping tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 2:
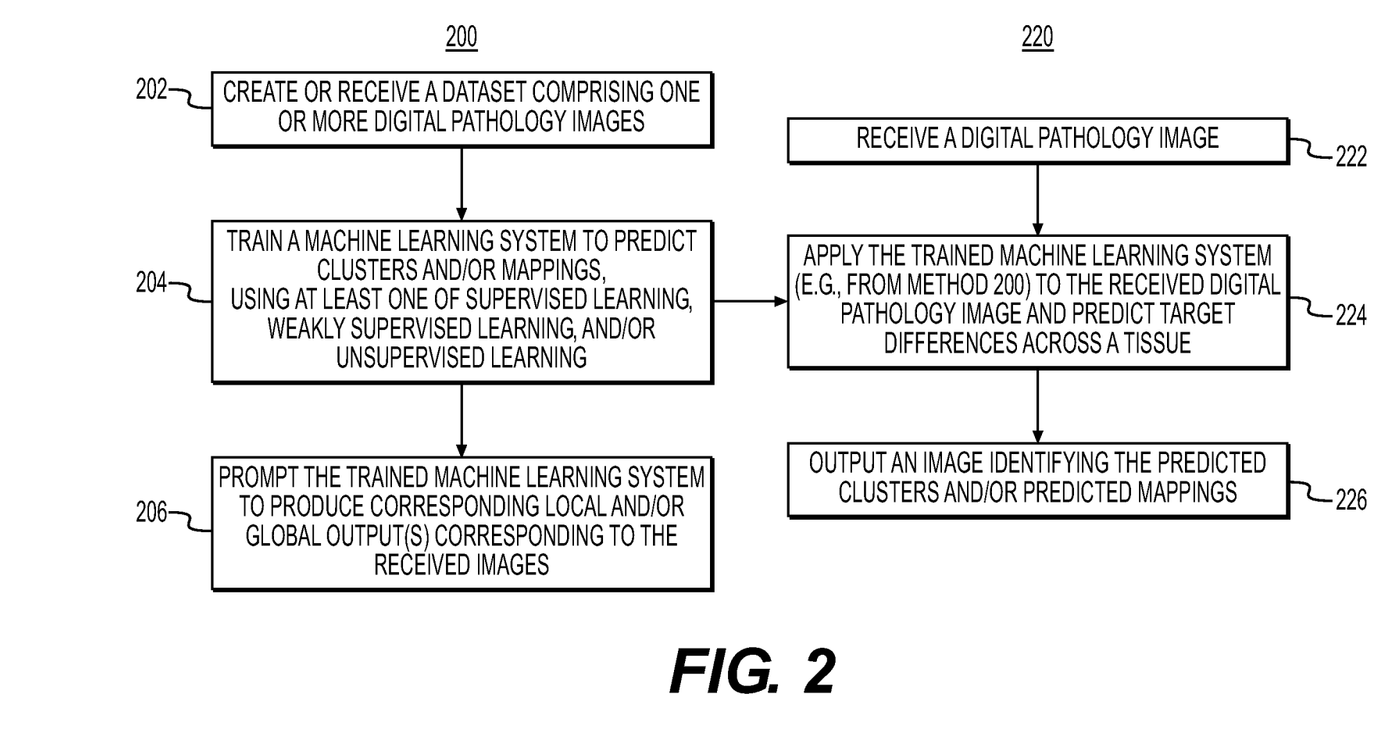
FIG. 2 is a flowchart of an exemplary method for grouping cells in a WSI that share similar targets, according to an exemplary embodiment of the present disclosure.

FIG. 2 is a flowchart illustrating exemplary methods (e.g., methods 200 and 220) for a tool for grouping cells in a WSI that share similar targets, using an AI system, according to an exemplary embodiment of the present disclosure. The method may include mapping one or more of predicted groupings to known biological targets using AI methods. The method may include using this grouping to take samples from the physical tissue specimen and sequence one or more of these groups. The method may include using this grouping to take samples from the physical tissue specimen for further analysis to detect physical and chemical characteristics of population of cells or particles such as flow cytometry, mass spectrometry, etc. The method may include using the spatial distribution and spatial relation of grouping of targets to determine treatment decisions by physicians and doctors. Inputs for the AI system may be WSIs and metadata. Outputs after training may be predicted clusters and/or predicted mappings. The predicted clusters may include (1) a set of points corresponding to the center of each antigen cluster found; and/or (2) a pixel mask that segments the image into antigen clusters. The predicted mappings may include (1) a map from any of the clusters to predicted antigens; and/or (2) for one or more of the clusters, a list of likely antigens.

Exemplary Cell Grouping Tool Development: An exemplary training method 200 (e.g., steps 202 to 206) may be performed by the cell grouping tool 101 automatically and/or in response to a request from a user (e.g., pathologist, patient, oncologist, technician, administrator, etc.). The exemplary method 200 for developing a cell grouping tool may include one or more of the steps below. In step 202, the method may include receiving a WSI and/or metadata. For example, the method may include receiving one or more digitized images of a pathology specimen (e.g., histology), related information (e.g., specimen type, available parts, gross description, etc.), clinical information (e.g., diagnosis, biomarker information, etc.), and/or patient information (e.g., demographics, gender, etc.). Additionally, data may be stored into a digital storage device (e.g., hard drive, network drive, cloud storage, RAM, etc.). In step 204, the method may include using image processing techniques, artificial intelligence, and/or machine learning, to predict clusters and mappings, using at least one of supervised learning, weakly supervised learning, and/or unsupervised learning. The supervised learning may include (a) inputting a collection of digital images of tissues with spatial transcriptomic/imaging mass cytometry techniques to get the spatial distribution of targets on tissue slides with high resolution; and/or (b) training a machine learning system for segmentation of predicting the ground truth spatial transcriptomic and/or genetic marker masks, e.g., convolutional neural network (CNN), fully convolutional neural network, U-Net to predict each pixel, super-pixel, and/or other region. The weakly supervised learning may include using knowledge about a presence or absence of targets in a slide, and using weakly supervised learning techniques such as Multiple instance Learning (MIL) to learn a segmentation for predicting these targets spatially. The unsupervised learning may include (a) using unsupervised or self-supervised learning techniques such as autoencoders or contrastive learning to learn and generate high-level embeddings for small regions of slides that encode morphological differences; and/or (b) using unsupervised clustering techniques such as k-means and/or Hierarchical Clustering to generate groupings of cells with similar morphological embeddings. In step 206, prediction results may be converted into a visual output depending on a type of user (e.g., pathologist, patient, oncologist, etc.), and the results may be displayed in a format based on the type of user and the use case (e.g., interactive, structured, templatized, static, etc.).

Exemplary Cell Grouping Tool Usage: An exemplary production method 220 (e.g., steps 222 to 226) may be performed by the cell grouping tool 101 automatically and/or in response to a request from a user (e.g., pathologist, patient, oncologist, etc.). The exemplary method 220 for using a cell grouping tool may include one or more of the steps below. In step 222, the method may include receiving one or more digitized images of a pathology specimen. In step 224, the method may include applying a trained machine learning system to the received digital pathology image and predicting target differences across a tissue. The method may include using the AI system's predicted segmentation together with a clustering heuristic to determine the best, or optimal beyond a threshold, places to sample to maximize the information gained about the target differences across the slide. The method may include using available sequencing techniques to find out the exact target composition of the samples, and using the segmentation to infer the spatial distribution over these factors in the slide. The method may include using flow cytometry and mass spectrometry techniques to determine the physical and chemical characteristics of the samples. The method may include using the spatial distribution and spatial relation of grouping of targets to determine treatment decisions by physicians and doctors. In step 226, the method may include outputting an image identifying the predicted target clusters and/or predicted mappings.

Figure 3A:
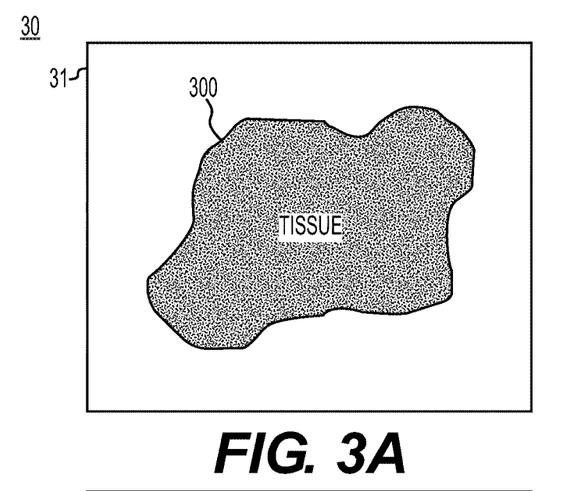
FIGS. 3A to 3D illustrate an exemplary usage method and an exemplary output for a cell grouping tool, according to an exemplary embodiment of the present disclosure.
Figure 3B:
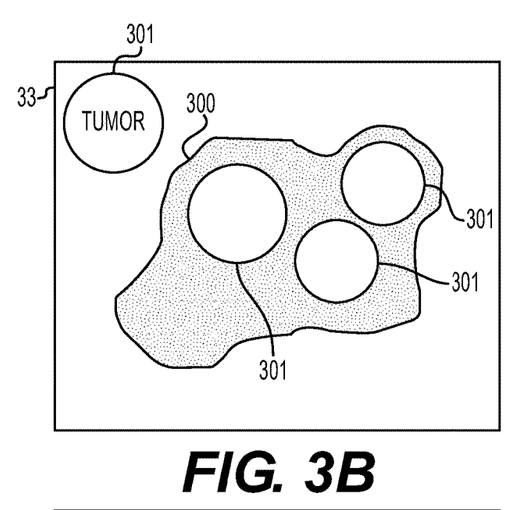
Figure 3C:
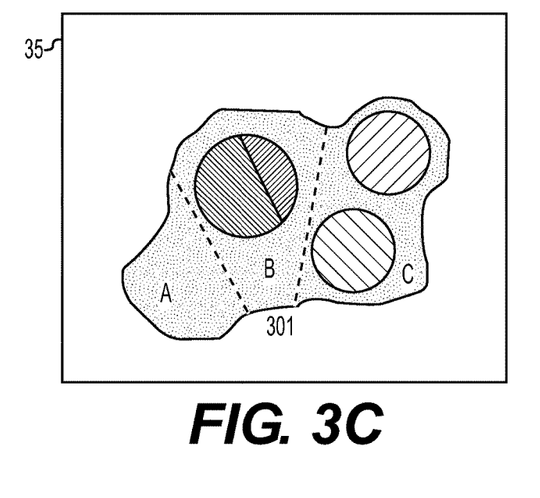
Figure 3D:
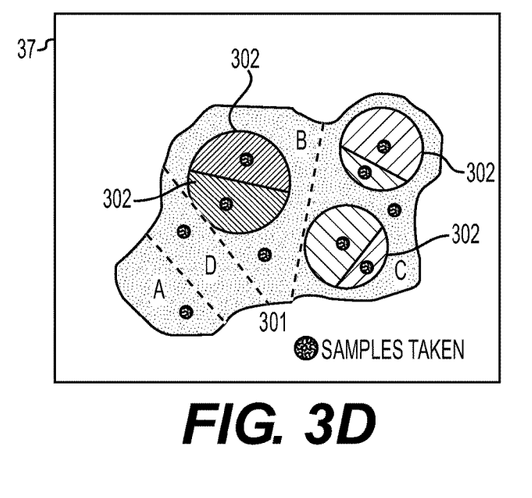

FIGS. 3A to 3D illustrate an exemplary usage method 30, including exemplary output 37 of the cell grouping tool. FIG. 3A illustrates step 31, which may input a WSI of a pathology specimen with a tissue 300 to the AI system. FIG. 3B illustrates tumors 301 located within the WSI. FIG. 3C illustrates the ground truth of the targets across both the tumor and benign tissue. The letters in FIG. 3C represent relevant target differences across benign tissue. FIG. 3D illustrates an output of the system after training that predicts the target clusters. The colors/shades in FIG. 3D represent the predictions of the different targets 302 across the tumor. The letters in FIG. 3D represent predicted relevant target differences across benign tissue. The samples taken may be used to identify a heterogeneity of the tissue (i.e., targeted sampling). According to FIGS. 3A to 3D, it is shown that a sufficiently sensitive system may allow the system to ensure each relevant region is sampled at least once.

Exemplary Embodiment for predicting and improving response to Chimeric Antigen Receptor T-Cell (CAR-T) treatment: Chimeric Antigen Receptor T-Cell treatment may include genetically modifying a patient's own T-cells to target antigens (e.g., CD19 and/or MR1) disproportionally present in the cell membranes of some cancers. This may be used to sample cancer tissue from a patient to evaluate what percentage of cancer cells have the target antigen and therefore predict if this is the right therapy for that patient. This may also be used to identify new and/or unique antigen targets for an individual patient, which may be more effective and have fewer side effects than other treatments. The input to the system may be an image and the output may be the clustering of antigens and/or predictions on clusters of antigens. The target for the AI system may be membrane protein clusters. Inputs for the artificial intelligence system may be WSIs and/or metadata. Outputs after training may be predicted clusters and/or predicted mappings. The predicted clusters may include (1) a set of points corresponding to the center of each antigen cluster found; and/or (2) a pixel mask that segments the image into antigen clusters. The predicted mappings may include (1) a map from any of the clusters to predicted antigens; and/or (2) for one or more of the clusters, a list of likely antigens.

Training method for predicting and/or improving response to CAR-T treatment: An exemplary method for training an AI system for predicting and/or improving response to CAR-T treatment may include supervised learning, weakly supervised learning, and/or semi-supervised learning. The supervised learning may include (a) using spatial transcriptomic techniques or imaging mass cytometry to get the spatial distribution over different antigens on different cancer and/or benign tissue (e.g., Barcoded Solid-Phase RNA Capture, Serial hybridization, fluorescent in situ hybridization (FISH), single-molecule FISH (smFISH), in situ sequencing, etc.), or manual annotations of cell types from the input WSI; and/or (b) training a machine learning system for the segmentation task of predicting this ground truth masks for each pixel in a slide. The weakly supervised learning may include using knowledge about the presence or absence of cell membrane antigens in a slide image, and using weakly supervised learning techniques such as MIL and/or variants thereof to learn a segmentation for predicting targets spatially. The semi-supervised learning may include (a) using unsupervised learning techniques such as autoencoders to learn and/or generate high level embeddings for small regions of a slides that encode morphological differences; (b) using antigen labels for a subset of this dataset to correlate tile embeddings to the presence or absence of specific membrane antigens; and/or (c) using this correlation to predict which cell embeddings are biologically most similar, or similar beyond a predetermined threshold, and/or predict whether certain groups of cells have the membrane antigen.

Usage method for predicting and/or improving response to CAR-T treatment: An exemplary usage method for the exemplary embodiment for predicting and/or improving response to CAR-T treatment may include (a) using region-based predictions or embeddings from the trained network and/or a clustering method such as k-means or hierarchical clustering to group regions of tissue that are predicted to share similar antigens by the system; (b) taking physical samples from the slide at these locations and/or using standard methods for antigen detection like enzyme immunoassays or latex agglutination on each sample; and/or (c) using the results from this detection, and regions grouped in step (a) to predict the relative proportions of the antigen across all cancer cells (or a portion thereof) and/or their spatial distribution.

Exemplary Embodiment as an alternative to immunohistochemistry (IHC) and/or fluorescence in situ hybridization (FISH) staining for human epidermal growth factor receptor 2 (HER2), estrogen receptor (ER), progesterone receptor (PR) expression detection: A target treatment today is done in breast cancers positive for a variety of proteins like HER2, ER and/or PR. These treatments require testing the cancer for the presence of these proteins, which is done by first ordering an IHC stain and if that is inconclusive, ordering the more expensive, time consuming FISH test. An exemplary embodiment may be used to make the process cheaper and/or more reliable. By using target sampling, it may not be necessary to re-stain and/or analyze the slide again. Simple tests for the presence or absence of the biomarkers in each of the samples tested may be sufficient to determine the presence of the biomarker across the whole tissue. The targets for the AI system may be HER2, ER, or PR status. Inputs for the AI system may be WSIs and/or metadata. Outputs for the AI system may be predicted clusters and/or predicted mappings. The predicted clusters may include (a) a set of points corresponding to the center of each biomarker cluster found; and/or (b) a pixel mask that segments the image into biomarker clusters. The predicted mappings may include (a) a map from any of the clusters to predicted biomarkers; and/or (b) for one or more of the clusters, a list of likely biomarker.

Training method for an alternative to IHC and/or FISH staining for HER2, ER, and PR expression detection: An exemplary method for training may include supervised learning, weakly supervised learning, and/or semi-supervised learning. The supervised learning may include (a) using a dataset of IHC and/or FISH stained slides to produce ground truth segmentations; and/or (b) training a CNN at the segmentation task of predicting this ground truth masks for each pixel in a slide. The weakly supervised learning may include using knowledge about the presence or absence of these biomarkers, and using weakly supervised learning techniques such as MIL to learn a segmentation for predicting these targets spatially. The semi-supervised learning may include (a) using unsupervised learning techniques such as autoencoders to learn and/or generate high level embeddings for small regions of a slides that encode morphological differences; (b) using IHCs or FISH labels for a subset of this dataset to correlate specific tile embeddings to the presence or absence of the biomarkers; and/or (c) using this correlation to predict which cell embeddings are biologically most similar, or similar beyond a predetermined threshold, and/or predict whether certain groups of cells have the biomarker.

Usage method for an alternative to IHC and/or FISH staining for HER2, ER, PR expression detection: An exemplary usage method may include (a) using region-based predictions or embeddings from the trained network and/or a clustering algorithm such as k-means or hierarchical clustering to group regions of tissue that are predicted to share similar biomarker concentrations by the system; (b) taking physical samples from the slide at these locations and/or using standard methods for biomarker detection on each sample; and/or (c) using the results from this detection, and regions grouped in step (a) to predict the relative proportions of the biomarker across some or all cancer cells and/or their spatial distribution.

Exemplary Embodiment as a complement and/or replacement of BRCA+HRD testing: For some types of cancers (e.g., ovarian cancer) a large percentage of cases may be attributed to a combination of germ line and/or tumor specific mutations that are well understood and may be used to treat patient more effective with adjuvant therapies (e.g., PARP inhibitors therapy). The testing required to confirm which kind of mutations occurred may require separate sequencing of tumor and/or germ line cells. Some tests may do this at a genetic level, which sometimes has problems acquiring enough read depth coverage for reliable heterozygous variant detection. This may provide spatial sampling of the tumor and/or germline cells that, depending on its efficacy, may aid or even replace the need for this expensive genetic based differentiation analyses. The target may include BRCA and/or HRD clusters. Inputs may include WSIs and/or metadata. Outputs may include predicted clusters and/or predicted mappings. Predicted clusters may include (a) a set of points corresponding to the center of each target cluster found; and/or (b) a pixel mask that segments the image into target clusters. Predicted mappings may include (a) a map from any of the clusters to predicted targets; and/or (b) for one or more of the clusters, a list of likely targets.

Training method as a complement and/or replacement of BRCA+HRD testing: An exemplary method for training may include defining genetic targets, e.g., presence/absence of germ line (e.g., BRCA1 and/or BRCA2) and/or tumor specific (e.g., ATM, BARD1, BRCA1, BRCA2, BRIP1) genes. The method may include supervised learning, weakly supervised learning, and/or semi-supervised learning. The supervised learning may include (a) using state of the art spatial transcriptomic techniques and/or selected examples of HRD testing to get the spatial distribution over the genetic targets on different cancer and/or benign tissue; and/or (b) training a CNN at the segmentation task of predicting this ground truth masks for each pixel in a slide. The weakly supervised learning may include, with knowledge about the genetic targets present in a slide, using weakly supervised learning techniques such as MIL to learn a segmentation for predicting these targets spatially. The semi-supervised learning may include (a) using unsupervised learning techniques such as autoencoders to learn and/or generate high level embeddings for small regions of a slides that encode morphological differences; (b) using genetic targets labels for a subset of this dataset to correlate tile embeddings to the presence or absence of specific membrane antigens; and/or (c) using this correlation to predict which cell embeddings are biologically most similar, or similar beyond a predetermined threshold, and/or predict whether certain groups of cells have the same genetic targets.

Usage method as a complement and/or replacement of BRCA+HRD testing: An exemplary usage method may include (a) using region-based predictions or embeddings from the trained network and/or a clustering algorithm such as k-means or hierarchical clustering to group regions of tissue that are predicted to share similar genetic targets by the system; (b) taking physical samples from the slide at these locations and/or using standard methods for HRD detection like TumorNext-HRD on each sample; and/or (c) using classical sequencing techniques that don't require genetic based differentiation of germline and/or tumor cells.

Exemplary embodiment for increasing sensitivity of tumor specific genetic assays: Some mutations (e.g., KRAS G12C) have been linked to a variety of different cancers that respond well to adjuvant treatments. Genetic assays used to detect these mutations, however, may require an allele copy frequency of at least 1%. An exemplary embodiment may be used to dramatically increase the effective sensitivity of these assays by providing effective sampling of the tumor that increase the percentage of the sample most likely to exhibit the mutation. It may also be used to determine whether the tumor is heterogeneous in this mutation and therefore predict the expected effectiveness of the adjuvant treatment. The target may include a mutation cluster. Inputs may include WSIs and/or metadata. Outputs may include predicted clusters and/or predicted mappings. Predicted clusters may include (a) a set of points corresponding to the center of each mutation cluster found; and/or (b) a pixel mask that segments the image into mutation clusters. Predicted mappings may include (a) a map from any of the clusters to predicted mutations; and/or (b) for one or more of the clusters, a list of likely mutation(s).

Training method for increasing sensitivity of tumor specific genetic assays: An exemplary method may include defining genetic targets, e.g., any mutation that is believed to be disproportionately present in a tumor such as, e.g., KRAS G12C. The method may include supervised learning, weakly supervised learning, and/or semi-supervised learning. The supervised learning may include (a) using state of the art spatial transcriptomic techniques and/or selected examples of HDR testing to get the spatial distribution over the genetic targets on different cancer and/or benign tissue; and/or (b) training a CNN at the segmentation task of predicting this ground truth masks for each pixel in a slide. The weakly supervised learning may include, with knowledge about the genetic targets present in a slide, using weakly supervised learning techniques such as MIL to learn a segmentation for predicting these targets spatially. The semi-supervised learning may include (a) using unsupervised learning techniques such as autoencoders to learn and/or generate high level embeddings for small regions of a slides that encode morphological differences; (b) using genetic targets labels for a subset of this dataset to correlate tile embeddings to the presence or absence of specific membrane antigens; and/or (c) using this correlation to predict which cell embeddings are biologically most similar, or similar beyond a predetermined threshold, and/or predict whether certain groups of cells have the same genetic targets.

Usage method for increasing sensitivity of tumor specific genetic assays: An exemplary usage method may include (a) using region-based predictions or embeddings from the trained network and/or a clustering algorithm such as k-means or hierarchical clustering to group regions of tissue that are predicted to share similar genetic targets by the system; and/or (b) taking physical samples from the slide at these locations and/or using standard genetic assays on each sample.

Exemplary embodiment for personalized treatment response testing: As more target treatment options become available, being able to only test one treatment at a time in a patient may become a limiting factor. One way to address this may be to take biopsies from a specific patient, grow this cancer tissue and/or test several treatments in parallel to choose which would most likely work best for the patient. Targeted sampling may be necessary to ensure all representative genotypes of a tumor are experimented on and may be used to efficiently test side effects on a representative sample of healthy tissue as well. The target may include treatment response clusters. Inputs may include WSIs and/or metadata. Outputs may include predicted clusters and/or predicted mappings. Predicted clusters may include (a) a set of points corresponding to the center of each target cluster found; and/or (b) a pixel mask that segments the image into target clusters. Predicted mappings may include (a) a map from any of the clusters to predicted targets; and/or (b) for one or more of the clusters, a list of likely targets.

Training method for personalized treatment response testing: An exemplary method for training may include, depending on what treatments are of interest to test response for, using any of the methods mentioned above in other embodiments or the general descriptions to train a system that may group cells in the clusters required for the test.

Usage method for personalized treatment response testing: An exemplary usage method may include (a) using the system above to select S samples across the patient's tumor and/or germ line cells to grow; (b) growing N sets of the S samples and apply the treatments of interest to a statistically representative number of sets, such that positive or negative results on that super set are statistically significant and/or indicate high likelihood of replicating the effects that would happen on the patient; (c) using this data to identify which treatment would be best for the patient; (d) administering the identified treatment to the patient; (e) using this procedure to monitor the amount and/or genetic distribution of the disease as treatment progresses; and/or (f) using this procedure in recurrent cases to understand the genetic composition of the recurrent cancer and/or specifically target it.

Exemplary embodiment as a complement or replacement of Tumor Mutation Burden (TMB), Tumor Inflammation Signature (TIS), and/or Microsatellite Instability-High (MSI-h): TMB, TIS and/or MSI-h are emerging pan-tumor biomarkers used to identify patients who are more likely to benefit from immunotherapies. These biomarkers are assessed through a gene panel and provide insights of the molecular interactions within the tumor microenvironment. An exemplary embodiment may provide spatial sampling of the tumor, mutation and/or inflammation in the tissue that contribute to these genomic biomarkers to help better understand the biology and further improve patient response. The target may include TMB, gene expression profile (GEP), and/or MSI-h clusters. Inputs may include WSIs and/or metadata. Outputs may include predicted clusters and/or predicted mappings. Predicted clusters may include (a) a set of points corresponding to the center of each target cluster found; and/or (b) a pixel mask that segments the image into target clusters. Predicted mappings may include (a) a map from any of the clusters to predicted targets; and/or (b) for one or more of the clusters, a list of likely targets.

Training method as a complement or replacement of Tumor Mutation Burden (TMB), Tumor inflammation signature (TIS), and/or Microsatellite Instability-High (MSI-h): An exemplary method for training may include defining genomic biomarker targets, e.g., presence/absence of TMB, TIS, and/or MSI-h biomarkers. The method may include supervised learning, weakly supervised learning, and/or semi-supervised learning. The supervised learning may include (a) using state of the art spatial transcriptomic techniques and/or selected examples of TMB, TIS and/or MSI testing to get the spatial distribution over the genetic targets on different cancer and/or benign tissue; and/or (b) training a machine learning system (e.g., CNN, fully convolutional network, etc.) on the segmentation task of predicting the ground truth masks for each pixel in a slide. The weakly supervised learning may include, with knowledge about the genetic targets present in a slide, using weakly supervised learning techniques such as MIL to learn a segmentation for predicting these targets spatially. The semi-supervised learning may include (a) using unsupervised learning techniques such as autoencoders to learn and/or generating high level embeddings for small regions of a slides that encode morphological differences; (b) using genetic targets labels for a subset of this dataset to correlate tile embeddings to the presence or absence of specific membrane antigens; and/or (c) using this correlation to predict which cell embeddings are biologically most similar, or similar beyond a predetermined threshold, and/or predict whether certain groups of cells have the same genetic targets.

Usage method as a complement or replacement of Tumor Mutation Burden (TMB), Tumor inflammation signature (TIS), and/or Microsatellite Instability-High (MSI-h): An exemplary usage method may include (a) using region-based predictions or embeddings from the trained network and/or a clustering algorithm such as k-means or hierarchical clustering to group regions of tissue that are predicted to share similar genetic targets by the system; (b) taking physical samples from the slide at these locations and/or using standard methods like IMPACT for TMB, TIS and/or MSI detection on each sample; and/or (c) classical sequencing techniques that may not require genetic based differentiation of germline and/or tumor cells.

Exemplary embodiment as an alternative to programmed cell death ligand 1 (PDL1) expression assessment: PDL1 is a biomarker being used to assess whether a patient will likely respond to immunotherapies. It is being tested through an IHC test and/or the presence of PDL1 in the tumor and/or in immune cells are being assessed by pathologists to determine patient's likelihood of response to these therapies which is qualitative and subjective. This may be used to determine and better understand patient's PDL1 expression patterns cheaper and more reliably. The target may include PDL1 stats in tumor and/or immune cells. Inputs may include WSIs and/or metadata. Outputs may include predicted clusters and/or predicted mappings. Predicted clusters may include (a) a set of points corresponding to the center of each target cluster found; and/or (b) a pixel mask that segments the image into target clusters. Predicted mappings may include (a) a map from any of the clusters to predicted target biomarkers; and/or (b) for one or more of the clusters, a list of likely target biomarkers.

Training method as an alternative to PDL1 expression assessment: An exemplary method for training may include supervised learning, weakly supervised learning, and/or semi-supervised learning. The supervised learning may include (a) using a dataset of IHC stained slides to produce ground truth segmentations; and/or (b) training a CNN at the segmentation task of predicting this ground truth masks for each pixel in a slide. The weakly supervised learning may include using knowledge about the presence or absence of PDL1 biomarkers, and using weakly supervised learning techniques such as MIL to learn a segmentation for predicting these targets spatially. The semi-supervised learning may include (a) using unsupervised learning techniques such as autoencoders to learn and/or generate high level embeddings for small regions of a slides that encode morphological differences; (b) using IHCs labels for a subset of this dataset to correlate specific tile embeddings to the presence or absence of the biomarkers; and/or (c) using this correlation to predict which cell embeddings are biologically most similar, or similar beyond a predetermined threshold, and/or predict whether certain groups of cells have the biomarker.

Usage method as an alternative to PDL1 expression assessment: An exemplary usage method may include (a) using region-based predictions or embeddings from the trained network and/or a clustering algorithm such as k-means or hierarchical clustering to group regions of tissue that are predicted to share similar biomarker concentrations by the system; (b) taking physical samples from the slide at these locations and/or using standard methods for biomarker detection on each sample; and/or (c) using the results from this detection, and regions grouped in step (a) to predict the relative proportions of the biomarker across all cancer cells and/or their spatial distribution.

One or more embodiments may be implemented within a clinical workflow at the hospital, lab, medical center as (1) Web application (cloud-based or on-premises); (2) Mobile application; (3) Interactive report; (4) Static report; and/or (5) Dashboard.

Figure 4:
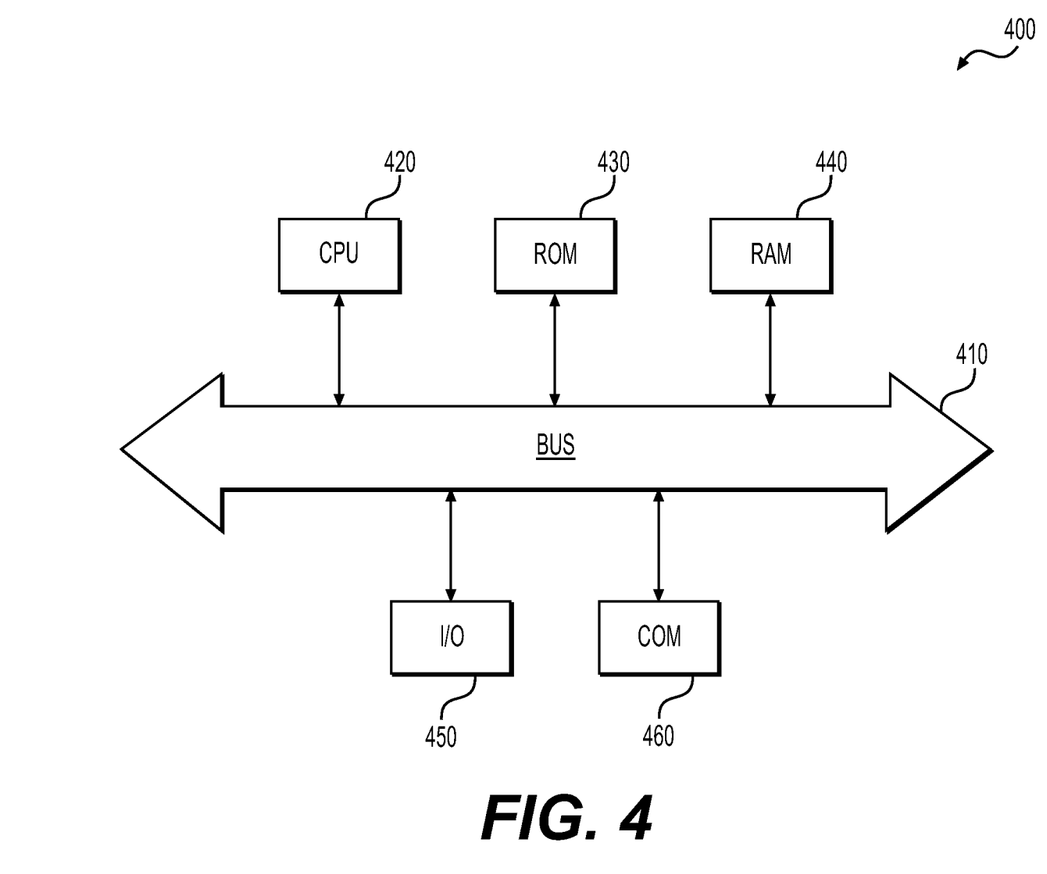
FIG. 4 depicts an example system that may execute techniques presented herein.

As shown in FIG. 4, device 400 may include a central processing unit (CPU) 420. CPU 420 may be any type of processor device including, for example, any type of special purpose or a general-purpose microprocessor device. As may be appreciated by persons skilled in the relevant art, CPU 420 also may be a single processor in a multi-core/multiprocessor system, such system operating alone, or in a cluster of computing devices operating in a cluster or server farm. CPU 420 may be connected to a data communication infrastructure 410, for example, a bus, message queue, network, or multi-core message-passing scheme.

Device 400 also may include a main memory 440, for example, random access memory (RAM), and also may include a secondary memory 430. Secondary memory 430, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and/or written to by the removable storage drive. As may be appreciated by persons skilled in the relevant art, such a removable storage unit generally includes a computer usable storage medium having stored therein computer software and/or data.

In alternative implementations, secondary memory 430 may include other similar means for allowing computer programs or other instructions to be loaded into device 400. Examples of such means may include a program cartridge and/or cartridge interface (such as that found in video game devices), a removable memory chip (such as an EPROM, or PROM) and/or associated socket, and other removable storage units and interfaces, which allow software and/or data to be transferred from a removable storage unit to device 400.

Device 400 also may include a communications interface ("COM") 460. Communications interface 460 allows software and/or data to be transferred between device 400 and external devices. Communications interface 460 may include a modem, a network interface (such as an Ethernet card), a communications port, a PCMCIA slot and card, or the like. Software and/or data transferred via communications interface 460 may be in the form of signals, which may be electronic, electromagnetic, optical, or other signals capable of being received by communications interface 460. These signals may be provided to communications interface 460 via a communications path of device 400, which may be implemented using, for example, wire or cable, fiber optics, a phone line, a cellular phone link, an RF link or other communications channels.

The hardware elements, operating systems and/or programming languages of such equipment are conventional in nature, and it is presumed that those skilled in the art are adequately familiar therewith. Device 400 also may include input and/or output ports 450 to connect with input and/or output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:

1. A method of targeted sampling, comprising:
   receiving one or more patient-specific medical images of a tissue sample of a patient;
   determining, by providing the patient-specific medical images to a machine learning system, one or more optimal tissue sampling locations within a target region among one or more target regions of the tissue sample to maximize information gained about the tissue sample, the target region being associated with a clinically relevant tissue feature; and
   providing the target region and the one or more optimal tissue sampling locations for output to a display.

2. The method of claim 1, further comprising:

receiving sequencing data of the tissue sample, the sequencing data indicating a target composition of one or more samples at the one or more optimal tissue sampling locations; and determining, using the machine learning system and based on the sequencing data, a spatial distribution of the optimal tissue sampling locations across the target region.

3. The method of claim 1, wherein the one or more optimal tissue sampling locations are determined using segmentation and a clustering heuristic.

4. The method of claim 1, wherein the one or more optimal tissue sampling locations comprise optimal genetic sampling locations.

5. The method of claim 1, wherein each of the one or more target regions corresponds to a different biomarker cluster.

6. The method of claim 1, further comprising:
determining, using the one or more target regions and the machine learning system, a mapping of each of the one or more target regions to a biological target; and
providing the biological target for output to the display.

7. The method of claim 1, further comprising:
determining, using the one or more target regions and the machine learning system, a mapping of each of the one or more target regions to a predicted mutation; and
providing the predicted mutation for output to the display.

8. The method of claim 1, further comprising:
determining, using the machine learning system, one or more pixel masks, each pixel mask corresponding to one of the target regions; and
providing the pixels masks for output to the display.

9. The method of claim 1, further comprising:
determining, based on a spatial distribution and spatial relation of the one or more target regions, a treatment decision associated with the patient.

10. The method of claim 1, further comprising:
determining, using flow cytometry and/or mass spectrometry techniques, one or more physical and/or chemical characteristics of one or more samples from the one or more determined optimal sampling locations.

11. The method of claim 1, wherein determining the one or more optimal tissue sampling locations is configured to maximize information gained about (i) heterogeneity across the tissue sample and/or (ii) one or more target differences across the tissue sample.

12. A system, comprising:
at least one memory storing instructions; and
at least one processor configured to execute the instructions to perform operations comprising:
receiving one or more patient-specific medical images of a tissue sample of a patient;
determining, by providing the one or more patient-specific medical images to a machine learning system, one or more optimal tissue sampling locations within a target region among one or more target regions of the tissue sample to maximize information gained about the tissue sample, the target region being associated with a clinically relevant tissue feature; and
providing the target region and the one or more optimal tissue sampling locations for output to a display.

13. The system of claim 12, the operations further comprising:
receiving sequencing data of the tissue sample, the sequencing data having been collected based on the target regions; and
determining, using the machine learning system and based on the sequencing data, a spatial distribution of the optimal tissue sampling locations across the target region.

14. The system of claim 12, wherein the one or more optimal tissue sampling locations are determined using segmentation and a clustering heuristic.

15. The system of claim 12, wherein each of the one or more target regions corresponds to a different biomarker cluster.

16. The system of claim 12, the operations further comprising:
determining, using the one or more target regions and the machine learning system, a mapping of each of the one or more target regions to a biological target; and
providing the biological target for output to the display.

17. The system of claim 12, the operations further comprising:
determining, using the one or more target regions and the machine learning system, a mapping of each of the target regions to a predicted mutation; and
providing the predicted mutation for output to the display.

18. The system of claim 12, the operations further comprising:
determining, using the machine learning system, one or more pixel masks, each pixel mask corresponding to one of the target regions; and
providing the one or more pixels masks for output to the display.

19. The system of claim 12, the operations further comprising:
determining, based on a spatial distribution and spatial relation of the one or more target regions, a treatment decision associated with the patient.

20. A non-transitory computer-readable medium storing instructions that, when executed by a processor, cause the processor to perform operations, the operations comprising:
receiving one or more patient-specific medical images of a tissue sample of a patient;
determining, by providing the one or more patient-specific medical images to a machine learning system, one or more optimal tissue sampling locations within a target region among one or more target regions of the tissue sample to maximize information gained about the tissue sample, the target region being associated with a clinically relevant tissue feature; and
providing the target region and the one or more optimal tissue sampling locations for output to a display.

* * * * *